(12) United States Patent
Seguin

(10) Patent No.: US 9,011,523 B2
(45) Date of Patent: Apr. 21, 2015

(54) PROSTHETIC LEAFLET ASSEMBLY FOR REPAIRING A DEFECTIVE CARDIAC VALVE AND METHODS OF USING THE SAME

(76) Inventor: Jacques Seguin, Gstaad (CH)

( * ) Notice: Subject to any disclaimer, the term of this patent is extended or adjusted under 35 U.S.C. 154(b) by 43 days.

(21) Appl. No.: 13/527,463

(22) Filed: Jun. 19, 2012

(65) Prior Publication Data

US 2012/0323313 A1   Dec. 20, 2012

Related U.S. Application Data

(60) Provisional application No. 61/498,991, filed on Jun. 20, 2011.

(51) Int. Cl.
*A61F 2/24* (2006.01)

(52) U.S. Cl.
CPC .............. *A61F 2/246* (2013.01); *A61F 2/2418* (2013.01); *A61F 2/2454* (2013.01)

(58) Field of Classification Search
CPC ....... A61F 2/24; A61F 2/2418; A61F 2/2475; A61F 2/2415; A61F 2/2433; A61F 2/2414; A61F 2/2409; A61F 2/2436; A61F 2/2412; A61F 2/246; A61F 2/2454; A61F 2/2403; A61F 2/2466; A61F 2002/2484; A61F 2002/249; A61M 25/104
USPC ............ 623/1.11, 2.11, 2.36, 900, 2.37, 2.12, 623/2.1, 2.17, 2.16, 2.38, 2.19, 1.26, 1.24, 623/2.33, 913, 2.15, 2.13, 2.14; 606/192, 606/194, 108
See application file for complete search history.

(56) References Cited

U.S. PATENT DOCUMENTS

| | | | |
|---|---|---|---|
| 4,490,859 A | 1/1985 | Black et al. | |
| 5,147,391 A | 9/1992 | Lane | |
| 5,376,114 A | 12/1994 | Jarvik | |
| 5,830,239 A | 11/1998 | Toomes | |
| 6,168,614 B1 | 1/2001 | Andersen et al. | |
| 6,269,819 B1 | 8/2001 | Oz et al. | |
| 6,461,382 B1 | 10/2002 | Cao | |
| 6,582,462 B1 | 6/2003 | Andersen et al. | |
| 6,613,086 B1 | 9/2003 | Moe et al. | |
| 6,911,043 B2 | 6/2005 | Myers et al. | |
| 7,037,333 B2 | 5/2006 | Myers et al. | |
| 7,077,862 B2 | 7/2006 | Vidlund et al. | |
| 7,399,315 B2 | 7/2008 | Iobbi | |
| 7,591,847 B2 | 9/2009 | Navia et al. | |
| 2005/0228495 A1 | 10/2005 | Macoviak | |

(Continued)

FOREIGN PATENT DOCUMENTS

| | | |
|---|---|---|
| WO | WO 2004/030568 A2 | 4/2004 |
| WO | WO 2010/106438 A2 | 9/2010 |

*Primary Examiner* — Jocelin Tanner
(74) *Attorney, Agent, or Firm* — Foley & Lardner LLP; Christopher C. Bolten; Nicola A. Pisano

(57) ABSTRACT

Methods and apparatus are provided for repairing or replacing a defective cardiac valve including a prosthetic leaflet assembly having an expandable frame with one or more anchors configured to engage a predetermined region of the defective cardiac valve in an expanded deployed state, and at least one prosthetic leaflet coupled to the expandable frame. The prosthetic leaflet assembly is configured such that the prosthetic leaflet is suspended within a flow path of the defective cardiac valve and coapts with, and improves functioning of, one or more native leaflets of the defective cardiac valve.

20 Claims, 10 Drawing Sheets

(56) References Cited

U.S. PATENT DOCUMENTS

| | | |
|---|---|---|
| 2006/0058871 A1 | 3/2006 | Zakay et al. |
| 2008/0033541 A1 | 2/2008 | Gelbart et al. |
| 2008/0065204 A1 * | 3/2008 | Macoviak et al. ........... 623/2.17 |
| 2008/0125860 A1 | 5/2008 | Webler et al. |
| 2012/0271398 A1 * | 10/2012 | Essinger et al. ............ 623/1.11 |

* cited by examiner

PROSTHETIC LEAFLET ASSEMBLY FOR REPAIRING A DEFECTIVE CARDIAC VALVE AND METHODS OF USING THE SAME

I. CROSS-REFERENCE TO RELATED APPLICATIONS

This application claims priority to U.S. Provisional Application No. 61/498,991, filed Jun. 20, 2011, the entire contents of which are incorporated herein by reference.

II. FIELD OF THE INVENTION

This application generally relates to apparatus and methods for performing transcatheter or minimally invasive repair of a defective cardiac valve, such as the mitral, tricuspid, and aortic valves.

III. BACKGROUND OF THE INVENTION

The human heart has four major valves which moderate and direct blood flow in the cardiovascular system. These valves serve critical functions in assuring a unidirectional flow of an adequate blood supply through the cardiovascular system. The mitral valve and aortic valve control the flow of oxygen-rich blood from the lungs to the body. The mitral valve lies between the left atrium and left ventricle, while the aortic valve is situated between the left ventricle and the aorta. Together, the mitral and aortic valves ensure that oxygen-rich blood received from the lungs is ejected into systemic circulation. The tricuspid and pulmonary valves control the flow of oxygen-depleted blood from the body to the lungs. The tricuspid valve lies between the right atrium and right ventricle, while the pulmonary valve is situated between the right ventricle and the pulmonary artery. Together the tricuspid and pulmonary valves ensure unidirectional flow of oxygen-depleted blood received from the right atrium towards the lungs.

Heart valves are passive structures composed of leaflets that open and close in response to differential pressures on either side of the valve. The mitral valve acts as the inflow valve to the left side of the heart. Blood flows from the lungs, where it absorbs oxygen, and into the left atrium. When the mitral valve opens, blood flows from the left atrium to the left ventricle. The mitral valve then closes to prevent blood from leaking back into the lungs when the ventricle contracts to pump blood out to the body. Whereas the aortic, pulmonary, and tricuspid valves have three leaflets, the mitral valve has only two leaflets.

These heart valves may be rendered less effective by congenital, inflammatory, or infectious conditions, or disease, all of which may lead to dysfunction of the valves over time. Such degradation may result in serious cardiovascular compromise or even death. Because the left ventricle drives systemic circulation, it generates higher pressures than the right ventricle, and accordingly the aortic and mitral valves are more susceptible to dysfunction, such as stenosis or regurgitation. A stenotic mitral valve may impede blood flow into the heart, causing blood to back up and pressure to build in the lungs. Consequently, the presence of a stenotic valve may make it difficult for the heart to increase the amount of blood pumped during exercise, producing shortness of breath under physical activity. Regurgitation occurs when the mitral valve leaflets do not coapt correctly, thus causing blood to leak backwards into the left atrium and lungs each time the heart pumps. Improper coaptation of the mitral valve leaflets thus requires the heart to pump more blood with each contraction to eject the necessary amount of blood for systemic circulation; a process called volume overload. Although the heart may compensate for this overload for months to years, provided the progression of the leakage comes gradually, the heart will eventually begin to fail, producing shortness of breath and fatigue. Mitral valve dysfunction is rarely caused by congenital conditions, but is largely the result of degenerative disease due to advancing age, disease, or infection.

Previously known medical treatments to address diseased valves generally involve either repairing the diseased native valve or replacement of the native valve with a mechanical or biological valve prosthesis. All previously-known valve prostheses have some disadvantages, such as need for long-term maintenance with blood thinners, the risk of clot formation, limited durability, etc. Accordingly, valve repair, when possible, usually is preferable to valve replacement. However, most dysfunctional valves are too diseased to be repaired using previously know methods and apparatus. Accordingly, a need exists for a prosthesis capable of assisting heart valve function that enables treatment of a larger patient population, while reducing the need to fully supplant the native heart valve.

For many years, the standard treatment for such valve dysfunction called for surgical repair or replacement of the valve during open-heart surgery, a procedure conducted under general anesthesia. An incision is made through the patient's sternum (sternotomy), and the heart is accessed and stopped while blood flow is rerouted through a heart-lung bypass machine. When replacing the valve, the native valve is excised and replaced with either a mechanical or biological prosthesis. However, these surgeries are prone to many complications and long hospital stays for recuperation.

More recently, transvascular techniques have been developed for introducing and implanting a replacement valve, using a flexible catheter in a manner less invasive than open-heart surgery. In such techniques, a replacement valve is mounted in a crimped state at the end of a flexible catheter, and then advanced through the blood vessel of a patient until the prosthetic valve reaches the implantation site. The valve then is expanded to its functional size at the site of the defective native valve, usually by inflating a balloon within where the valve has been mounted. By expanding the prosthetic valve, the native valve leaflets are generally pushed aside and rendered ineffective. Examples of such devices and techniques, wherein the native valve is replaced in its entirety by a substitute tissue valve, are described, for example, in U.S. Pat. Nos. 6,582,462 and 6,168,614 to Andersen et al.

Mitral valve repair has become increasingly popular due to its high rates of success and the clinical improvements noted after repair. Several technologies have been developed to make mitral repair less invasive. These technologies range from iterations of the Alfieri stitch procedure; to coronary sinus-based modifications of mitral anatomy; to subvalvular placations or ventricular remodeling devices, which also may be employed to correct mitral valve regurgitation. Unfortunately, for a significant percentage of patients, mitral valve replacement is still necessary due to stenosis or anatomical limitations, and few less-invasive options are available for replacement procedures.

Prostheses have been produced and used for over forty years to treat cardiac disorders. They have been made from a variety of materials, both biological and artificial. Mechanical or artificial valves generally are made from non-biological materials, such as plastics or metals. Such materials, while durable, are prone to blood clotting and thrombus formation, which in turn increases the risk of embolization and stroke or ischemia. Anticoagulants may be taken to prevent blood clotting that may result in thromboembolic complications and catastrophic heart failure, however, such anti-clotting medication may complicate a patient's health due to the increased risk of hemorrhage.

In contrast, "bio-prosthetic" valves are constructed with leaflets made of natural tissue, such as bovine, equine or porcine pericardial tissue, which functions very similarly to the leaflets of the natural human heart valve by imitating the natural action of the heart valve leaflets, coapting between adjacent tissue junctions known as commissures. The main advantage of valves made from tissue is they are not as prone to blood clots and do not absolutely require lifelong systemic anticoagulation. A major disadvantage of tissue valves is they lack the long-term durability of mechanical valves. This is so because naturally occurring processes within the human body may stiffen or calcify the tissue leaflets over time, particularly at high-stress areas of the valve such as at the commissure junctions between tissue valve leaflets and at the peripheral leaflet attachment points, or "cusps," at the outer edge of each leaflet. Furthermore, valves are subject to stresses from constant mechanical operation within the body. In particular, the leaflets are in tension when in a closed position and are in compression when in an open position. Such tension causes prosthetic valves to wear out over time, requiring replacement.

In recent years, bio-prosthetic valves have been constructed by integrating valve leaflets made from natural tissue into the stent-like supporting frame, which provides a dimensionally stable support structure for the valve leaflets. In more advanced prosthetic heart valve designs, besides providing dimensionally stable support structure for the valve leaflets, the stent-like supporting frame also imparts a certain degree of controlled flexibility, thereby reducing stress on the leaflet tissue during valve opening and closure and extending the lifetime of the leaflets. In most designs, the stent-like supporting frame is covered with a biocompatible cloth (usually a polyester material such as Dacron™ or polytetrafluoroethylene (PTFE)) that provides sewing attachment points for the leaflet commissures and leaflets themselves. Alternatively, a cloth-covered suture ring may be attached to the stent-like supporting frame, providing a site for sewing the valve structure in position within the patient's heart during a surgical valve replacement procedure.

While iterative improvements have been made on surgical bioprosthetic valves over the last several decades, existing bioprosthetic valves still have drawbacks. One drawback is the mismatch in size and mass between opposing surfaces of the stent-like supporting frame. The mismatch is often due to the variability in the shapes and mechanical characteristics of the stent-like supporting frame. For prosthetic valves with balloon-expandable stent-like supporting frames, the recoil of the supporting frames post-balloon-inflation may lead to perivalvular leaks around the circumference of the prosthetic valve and potential slippage and migration of the valve post-implantation. Another risk associated with prosthetic valves having balloon-expandable supporting frames is potential damage to the leaflets of the prosthesis during implantation, when the leaflets may be compressed between the balloon and the supporting frame. For prosthetic valves with self-expanding stent-like supporting frames, mismatch may arise due to the deformation/movement of the supporting frame, e.g., slight deformation of the frame into a less than circular shape during normal cardiac movement. Such mismatch may lead to instability among components of a prosthetic valve, resulting in perivalvular leaks and uneven stress distribution in the valve leaflets, resulting in accelerated wear of the valve.

Another drawback in the construction of existing bio-prosthetic valves with self-expanding supporting frames is the potential for damage to the leaflet tissue arising from the spacing between the struts of the frame. For example, when the stent-like supporting frame is deployed, the distance between struts during expansion of the frame may stretch both the surrounding tissue and the leaflet tissue further apart than designed, potentially resulting in damage to surrounding tissue and leaflet tissue. With use of an oblong or circular radially self-expanding frame applied on the majority of the mitral valve, there is risk of left-ventricular outflow tract (LVOT) obstruction.

A mitral valve regurgitation often arises due to mitral annulus dilatation, which may be treated using a surgical technique to narrow and restore the natural shape the annulus. Usually the mitral valve and annulus are shaped like a "D", but when dilated the shape becomes more like an "O". Prosthetic annuloplasty rings are therefore an important additional component in some mitral valve repair techniques. A primary role of the annuloplasty ring is to reduce the size of the annulus and decrease the tension on the sutures while providing flexibility and mobility at the same time. An annuloplasty ring thus is omitted during mitral valve repair only exception in cases of infective endocarditis, in order to avoid excess foreign material. When an annuloplasty ring is used, three months of anticoagulation is often prescribed.

One recent technique for correcting mitral valve leakage, as described for example in U.S. Pat. No. 6,269,819 to Oz et al., employs a percutaneously placed catheter to introduce a clipping apparatus into a leaking mitral valve. Once positioned, the clip arms are unfolded and advanced into the left ventricle below the valve leaflets, after which it is retracted and closed over the leaflets, holding them together to reduce mitral regurgitation. If further improvements to regurgitation are to be made, the clip is released and further advanced for repositioning. Once decrease of leakage has been assessed, the clip is deployed to entrap together the free edges of the mitral leaflets, and the catheter withdrawn. The clip may be made of metal with a polyester fabric covering to promote healing. Because the clip transforms the mitral orifice into two orifices, the clip may significantly obstruct the flow of blood through the valve.

In view of the above-noted drawbacks of previously-known systems, it would be desirable to provide a device, and methods of using the same, that assists the functioning of the native cardiac valve, rather than removing or entirely supplanting the native valve. The native structures (mitral leaflets, chordae, papillary muscles, etc.) play an important role in left-ventricular function and therefore any valve replacement system that does not respect these elements may adversely impact the left-ventricular function.

It would also be desirable to provide a device having prosthetic leaflets, and methods of using the same that reduces tension on the prosthetic leaflets, thereby increasing the life of the prosthesis.

It further would be desirable to provide a device having a support frame, and methods of using the same, wherein the prosthesis is configured to firmly anchor to the native valve when deployed, without deformation or movement of the supporting frame at the annulus, thus reducing the risk of perivalvular leakage.

It still further would be desirable to provide a device, and methods of using the same, that may be deployed with reduced risk of obstructing blood flow relative to previously known mitral valve repair techniques.

IV. SUMMARY OF THE INVENTION

The present invention provides leaflet assembly prostheses, and methods of using the same, that overcomes the drawbacks of previously-known systems. In particular, the present invention provides a prosthetic leaflet assembly that may be suspended within the flow path of a defective cardiac valve to improve functioning of the native valve, while retaining much of the native valve structure and function. Exemplary embodiments of the inventive prosthetic leaflet assembly include an expandable frame and one or more prosthetic leaflets coupled to the frame. The expandable frame may be configured to transition from a contracted delivery state to an expanded deployed state and may have one or more anchors configured to engage a predetermined region, e.g., commissural area, of the defective cardiac valve in the expanded deployed state. Advantageously, the prosthetic leaflet assembly is configured such that one or more prosthetic leaflets are suspended within a flow path of the defective cardiac valve and coapt therewith, thereby improving functioning of the native valve.

The expandable frame may further include at least one stabilization member and at least one biasing member. The stabilization member may be disposed upstream of the defective native cardiac valve and configured to prevent the one or more native leaflets from prolapsing when the leaflets are subjected to backpressure, and also to prevent migration of the prosthetic leaflet assembly. The biasing member may be configured to urge the one or more anchors into engagement with the predetermined region(s). Additionally, the expandable frame and the prosthetic leaflets may be configured to self-expand between a delivery state enabling transcatheter delivery and an expanded, deployed state.

In accordance with one aspect of the invention, the prosthetic leaflet assembly may be implanted using a transvascular approach. Illustratively, implantation of a mitral valve embodiment of the present invention, for example, may be accomplished by passing a catheter through the femoral vein into the right atrium, followed by a transeptal puncture to gain access to the mitral valve from above. Alternatively, implantation may be accomplished by passing the catheter through the femoral artery into the aorta and through the aortic valve to gain access to the mitral valve from below. As yet another alternative, a minimally-invasive approach may be employed in which a catheter is inserted through a keyhole opening in the chest and then transapically from below the mitral valve. As yet a further alternative, an open heart surgery approach may be used to gain access to the mitral valve. Notably, the prosthetic leaflet assembly may be used with any cardiac valve including tricuspid valve, aortic valve, and pulmonary valve.

In some embodiments the prosthetic leaflet assembly may comprise a metal alloy, e.g., nickel-titanium, or polymer frame covered by animal tissue or synthetic fabric that mimics the leaflet valve configuration of the valve being repaired. The expandable frame of the prosthetic leaflet assembly may comprise the metal alloy or polymer frame and the leaflet assembly may comprise the animal tissue or synthetic fabric.

In accordance with one aspect of the present invention, a prosthetic leaflet assembly system is configured so as to enable subsequent implantation of a previously-known replacement valve, such that the replacement valve may be secured to the prosthetic leaflet assembly. The replacement valve may be implanted seconds, days, months, or years after the prosthetic leaflet assembly is deployed, e.g., if the repaired valve undergoes further deterioration due to disease progression or aging.

In accordance with another aspect of the present invention, an exemplary catheter is provided for delivering a prosthetic leaflet assembly transvascularly or transapically into a defective cardiac valve. The catheter may include a tube having an internal lumen, a stylet disposed within the internal lumen, and a suture disposed within the internal lumen. The suture may engage the prosthetic leaflet assembly when the prosthetic leaflet assembly is disposed within the internal lumen in a contracted delivery state. The stylet may have an end cap disposed at its distal end that may contact the distal end of the tube in the contracted delivery state. The catheter may further include a suture tube disposed within the internal lumen through which the suture may be disposed. The catheter may have a locking member disposed at the proximal end of the tube configured to lock the suture in place.

Methods of using the prosthetic leaflet assembly and system of the present invention also are provided.

V. BRIEF DESCRIPTION OF THE DRAWINGS

FIGS. 1A, 1B, and 1C depict an exemplary embodiment of a prosthetic leaflet assembly constructed in accordance with the principles of the present invention, suitable for use in mitral valve repair, wherein FIG. 1A is a perspective view, FIG. 1B is a bottom view, and FIG. 1C is an elevation front view.

FIGS. 2A through 2E are illustrative views of an exemplary expandable frame of the prosthetic leaflet assembly constructed in accordance with the principles of the present invention, wherein FIG. 2A is an elevation view, FIG. 2B is a perspective view, FIG. 2C is a top view, FIG. 2D is a side view, and FIG. 2E is a bottom view.

VI. DETAILED DESCRIPTION OF THE INVENTION

Figure 1A:
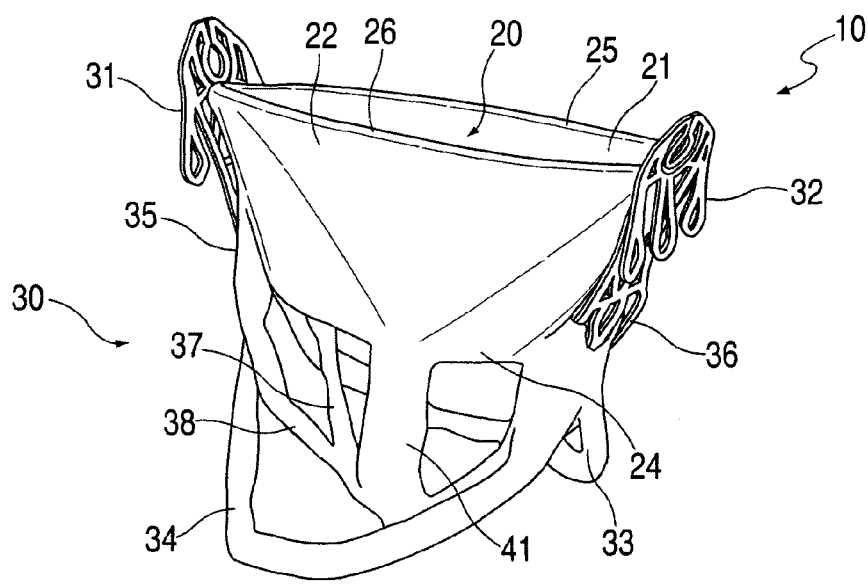
Figure 1B:
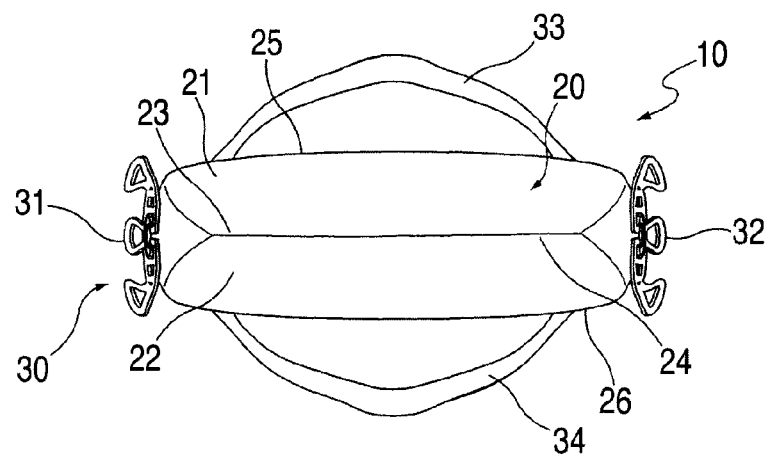
Figure 1C:
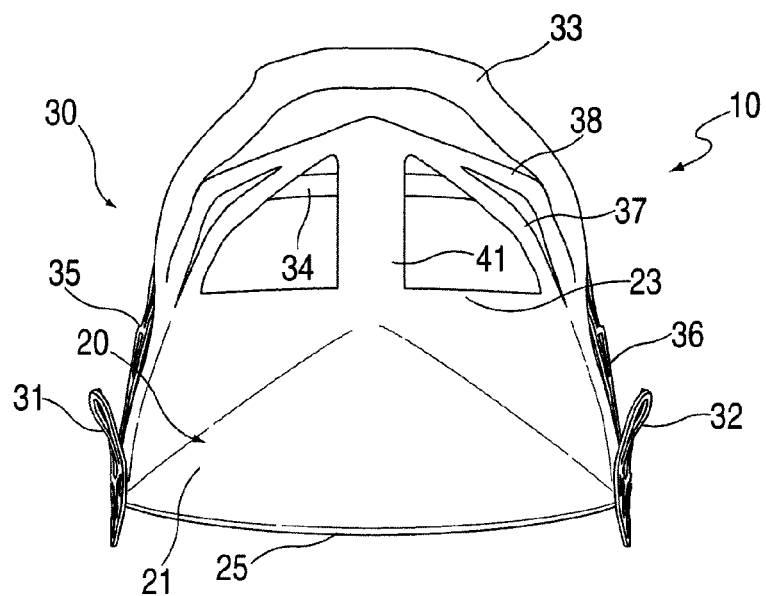
Figure 2A:
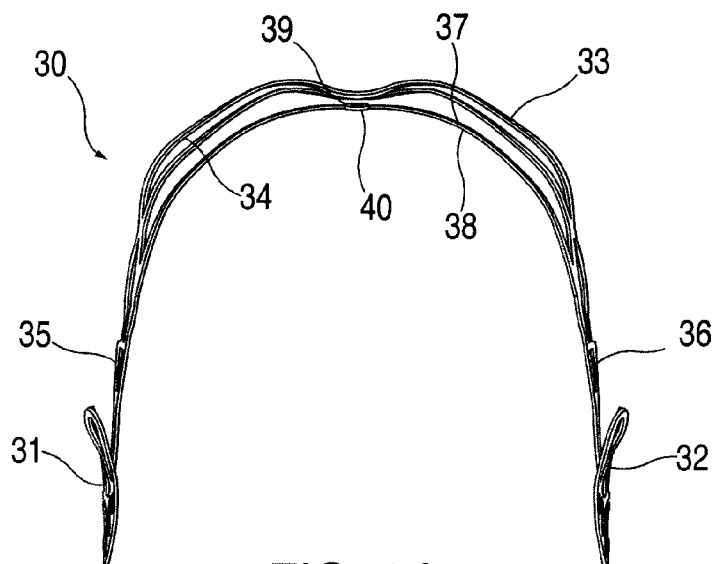
Figure 2B:
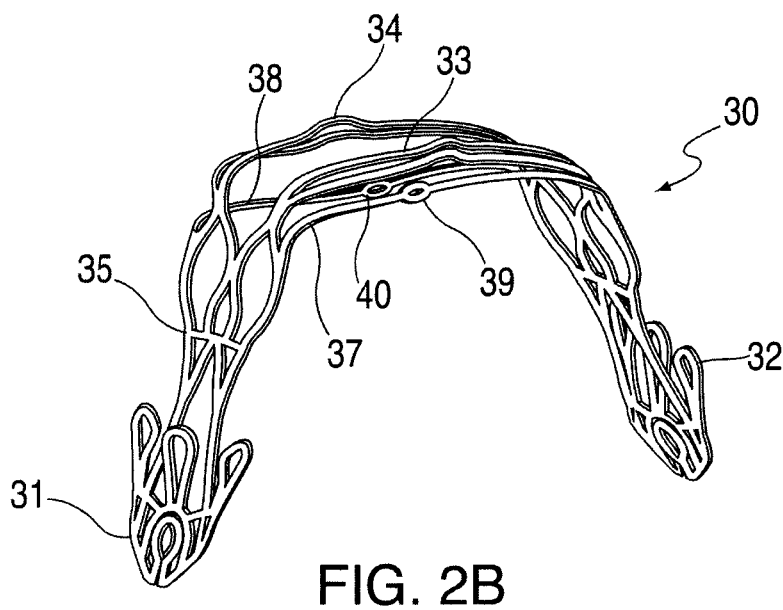
Figure 2C:
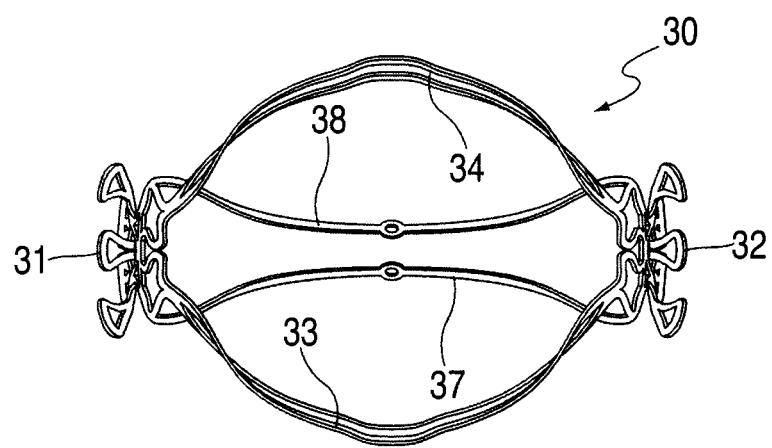
Figure 2D:
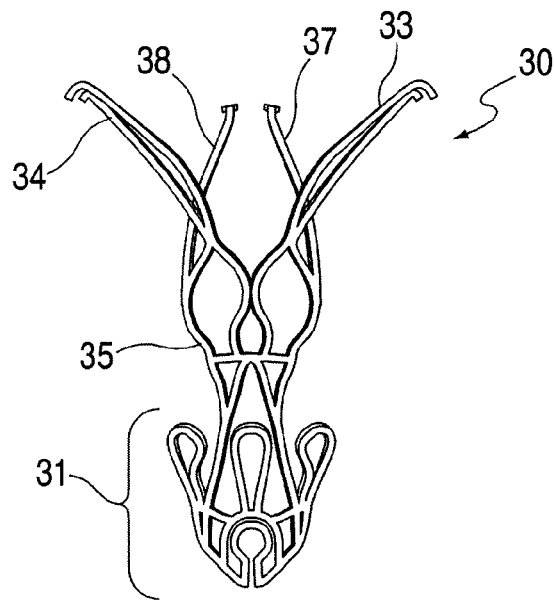
Figure 2E:
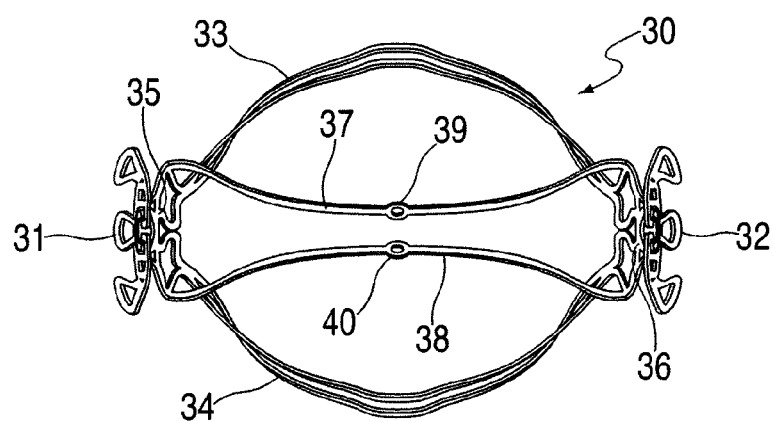

Referring to FIGS. 1A, 1B and 1C, an illustrative embodiment of a prosthetic leaflet assembly in accordance with the principles of the present invention is described. Illustratively, the prosthetic leaflet assembly is designed for repairing a defective mitral valve, although it could be readily adapted for other cardiac valves such as the tricuspid valve, aortic valve, or pulmonary valve. In FIG. 1A, prosthetic leaflet assembly 10 is shown "upside down", such that the leaflets (at the top of the figure) are configured to be positioned to extend into a patient's left ventricle, while the support members (at the bottom of the figure) preferably are configured to be disposed in the left atrium, above the native leaflets. Prosthetic leaflet assembly 10, includes animal tissue or synthetic leaflet assembly 20 mounted on expandable frame 30. As further described below, prosthetic leaflet assembly 10 preferably is configured to transition between an expanded, deployed state and a contracted delivery state, such that the device may be disposed within a delivery catheter for transvascular or minimally-invasive surgical delivery.

Leaflet assembly 20 illustratively includes first and second prosthetic leaflets 21 and 22 that may be coupled to expandable frame 30 between first and second anchors 31 and 32 using sutures or biocompatible adhesive. First prosthetic leaflet 21 has base 23 and free margin 25 and second prosthetic leaflet 22 has base 24 and free margin 26. Base 23 substantially contacts base 24 when leaflet assembly 20 is closed as illustrated in FIG. 1B. Prosthetic leaflets 21 and 22 may be configured such that the length of bases 23 and 24 of each leaflet is inferior to the length of free margins 25 and 26, thereby inducing prosthetic leaflets 21 and 22 to bend inward under forward blood flow, thereby improving the transprosthetic gradient, and outward during retrograde blood flow, improving coaptation of each prosthetic leaflet with the opposing corresponding native cardiac leaflet as described further below.

Leaflet assembly 20, including leaflets 21 and 22, preferably comprise treated animal tissue, such as porcine, bovine, or equine pericardial tissue fixed using glutaraldehyde as is per se known in the art of prosthetic valve design. Alternatively, leaflet assembly 20, including leaflets 21 and 22 may comprise any of a number of synthetic fabrics, such as a polyethylene terephthalate fabric, e.g., DACRON® (a registered trademark of Invista North America S.A.R.L. Corporation). As a further alternative, portions of leaflet assembly 20 may comprise synthetic material, while other portions, such as leaflets 21 and 22, may comprise animal tissue.

Although leaflet assembly 20 illustratively includes two prosthetic leaflets, fewer or more leaflets may be included without departing from the scope of the present invention. For example, in an embodiment wherein the prosthetic leaflet assembly is configured for repairing a defective aortic valve, the leaflet assembly may include three prosthetic leaflets. As another example, in an embodiment wherein one native leaflet is substantially dysfunctional, the prosthetic leaflet assembly may be designed in a semicircular configuration having a leaflet assembly including one prosthetic leaflet.

As best shown in FIGS. 2A through 2E, in an embodiment suitable for repairing a mitral valve, expandable frame 30 may include first and second anchors 31 and 32, first and second stabilization members 33 and 34, first and second body support members 35 and 36, first and second biasing members 37 and 38, and first and second attachment members 39 and 40. Expandable frame 30 may be configured for implantation in a circular-shaped or oval-shaped cardiac valve and may comprise a superelastic material, such as a nickel-titanium alloy. The superelastic material may be treated to expand from a contracted delivery state to an expanded deployed state as is well-known in the art for such materials. Alternatively, expandable frame 30 may comprise non-superelastic metal alloy, such as stainless steel or cobalt-chrome alloy, that may be compressed onto a balloon catheter and then plastically expanded during deployment. Expandable frame 30 may be covered with treated animal tissue or any of a number of synthetic fabrics using sutures or biocompatible adhesive.

Anchors 31 and 32 may be configured to engage predetermined region(s) or surface(s) within a patient's heart, such as the commissural areas of the defective cardiac valve, to anchor prosthetic leaflet assembly 10 at a desired location within the native valve structure. Beneficially, anchors 31 and 32 firmly anchor prosthetic leaflet assembly 10 to the native cardiac valve and move relatively with the motion of the native valve. Because leaflet coaptation is insured by leaflet assembly 20, the risk of perivalvular leakage is reduced.

First anchor 31 is coupled to first body support member 35 and second anchor 32 is coupled to second body support member 36. Body support members 35 and 36 may be coupled to stabilization members 33 and 34 and biasing members 37 and 38. Stabilization members 33 and 34 preferably are configured to be disposed upstream of the defective cardiac valve, so as prevent the native leaflets from ballooning or prolapsing during backflow and to prevent prosthetic leaflet assembly 10 migration.

Biasing members 37 and 38 preferably are configured to urge anchors 31 and 32 into engagement with the predetermined region, such as the commissural areas, when prosthetic leaflet assembly 10 is deployed. Biasing members 37 and 38 further may be configured to urge anchors 31 and 32 in a specified direction to further ovalize or modify the annulus of the defective cardiac valve, thereby moving the native leaflet closer to the center of the valve and enhancing coaptation with prosthetic leaflets 21 and 22 as described below.

First biasing member 37 may include attachment member 39 and second biasing member may include attachment member 40. Attachment members 39 and 40, illustratively eyelets, are configured to attach leaflet assembly 20 to expandable frame 30 with center attachment member 41, shown in FIG. 1C. Center attachment member 41 may comprise animal tissue or synthetic fabric, and may be coupled to attachment members 39 and 40 and leaflet assembly 20 using sutures or biocompatible adhesive. Alternatively, leaflet assembly 20 and center attachment member 41 may comprise a single piece of material.

Preferably, prosthetic leaflet assembly 10 is configured such that prosthetic leaflets 21 and 22 coapt with, and improve function of, one or more native leaflets of the defective cardiac valve, for example, during backpressure. In one embodiment, prosthetic leaflets 21 and 22 are configured to cover between 5 to 35 percent of the central opening of the native cardiac valve. Advantageously, prosthetic leaflet assembly 10 works together with the native cardiac valve, rather than pushing the leaflets of the native cardiac valve aside and rending the native valve structures ineffective. Additionally, stabilization members 33 and 34 and biasing members 37 and 38 are positioned away from the path of the native cardiac leaflets, thus reducing the risk of obstructing blood flow through the cardiac valve.

Figure 3:
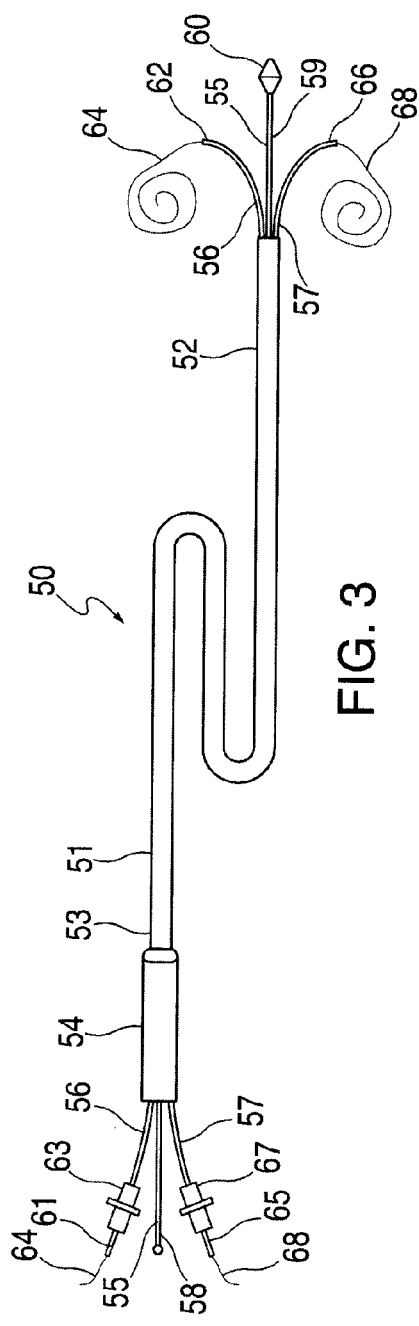
FIG. 3 depicts illustrative embodiments of a catheter for transvascular delivery of the prosthetic leaflet assembly of the present invention.

Referring now to FIG. 3, an exemplary embodiment of a delivery catheter for the prosthetic leaflet assembly of the present invention is described. Delivery catheter 50 includes a suitable length of tubing 51 having distal end 52, proximal end 53, an internal lumen extending therebetween, handle portion 54, stylet 55 disposed in the internal lumen, and first and second suture tubes 56 and 57 disposed in the internal lumen. Stylet 55 preferably has a length greater than that of tubing 51 and includes proximal end 58, distal end 59, and end cap 60 disposed at distal end 59. Stylet 55 and end cap 60 optionally may include a guide wire lumen extending throughout to accommodate passage of a guide wire. First suture tube 56 includes a length of tubing that may be greater than the length of tubing 51 and has proximal end 61, distal end 62, an internal lumen extending therebetween, and locking member 63 disposed near proximal end 61. First suture 64 is disposed in the internal lumen of first suture tube 56 and preferably has a length at least twice the length of first suture tube 56. Second suture tube 57 includes a length of tubing that may be greater than the length of tubing 51 and has proximal end 65, distal end 66, an internal lumen extending therebetween, and locking member 67 disposed near proximal end 65. Second suture 68 is disposed in the internal lumen of second suture tube 57 and preferably has a length at least twice the length of second suture tube 57. In one embodiment, first and second sutures 64 and 68 are each a single wire having a locking mechanism disposed at the respective distal end to engage into a matching locking mechanism on prosthetic leaflet assembly 10, e.g., on body support members 35 and 36. In another embodiment, first and second sutures 64 and 68 may be used as a lanyard to re-secure prosthetic leaflet assembly 10 to delivery catheter 50.

Delivery catheter 50 preferably comprises materials conventionally used in catheter designs, and has lengths and profiles suitable for the selected access path, i.e., either transvascular or transapical. Tubing 51 is sized to permit prosthetic leaflet assembly 10 to be compressed within, and retained within, delivery catheter 50 for delivery. In one embodiment, expandable frame 30 is self-expanding and causes prosthetic leaflet assembly 10 to expand when deployed. In an alternative embodiment, such as for plastically deformable embodiments of expandable frame 30, stylet 55 may include an expandable balloon or mandrel configured, as is conventional in the art of balloon-catheters, to be inflated to cause prosthetic leaflet assembly 10 to expand when deployed.

Figure 4A:
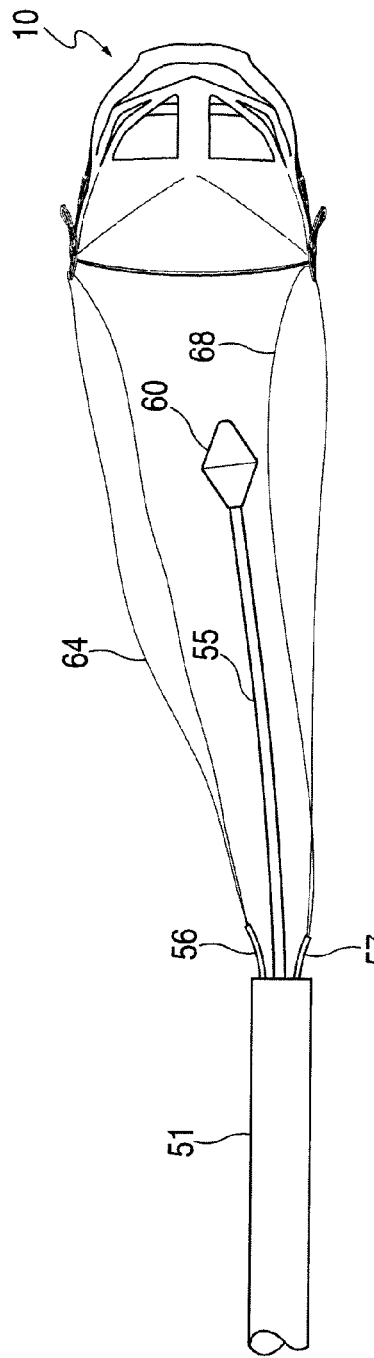
FIGS. 4A through 4D are illustrative views showing loading of the prosthetic leaflet assembly into the delivery catheter in accordance with aspects of the present invention.

Referring to FIGS. 4A through 4D, an exemplary method of loading the prosthetic leaflet assembly into the delivery catheter is now described. As depicted in FIG. 4A, the distal end of first suture 64 is looped around a portion of prosthetic leaflet assembly 10, illustratively the first anchor, and fed into distal end 62 of first suture tube 56 until the distal end of first suture 64 passes through the opening at proximal end 61 of first suture tube 56. With both ends of first suture 64 exposed at proximal end 61, locking member 63 is activated to lock first suture 64 in place. The distal end of second suture 68 then is looped around a portion of prosthetic leaflet assembly 10, illustratively the second anchor, and fed into distal end 66 of second suture tube 57 until the distal end of first suture 68 passes through the opening at proximal end 65 of second suture tube 57. With both ends of second suture 68 exposed at proximal end 65, locking member 67 is activated to lock second suture 68 in place.

Figure 4B:
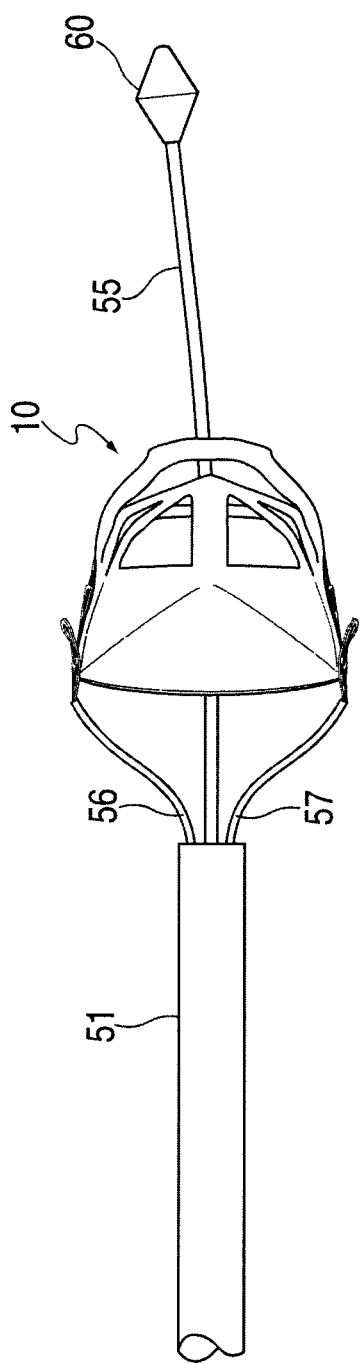
Figure 4C:
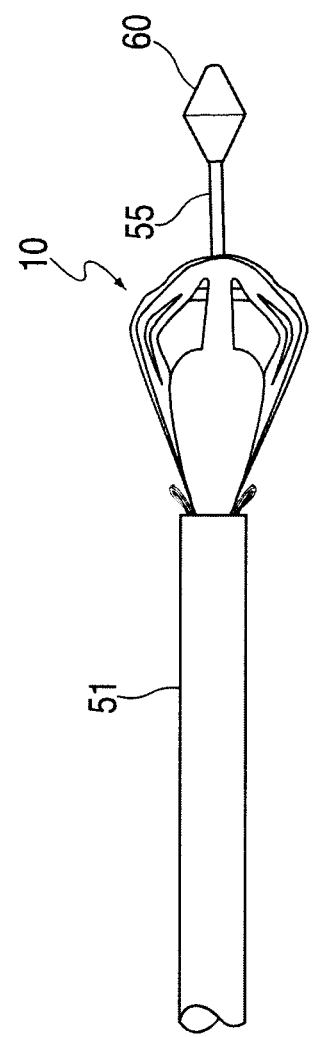
Figure 4D:
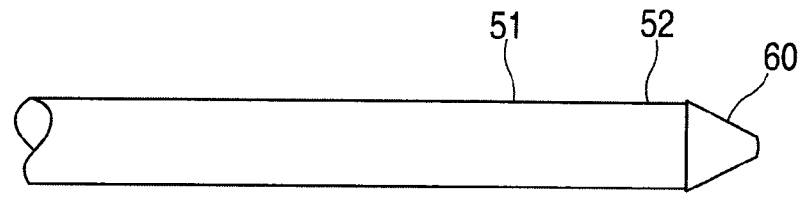

Next, proximal ends 61 and 65 of first and second suture tubes 56 and 57 are pulled proximally to urge prosthetic leaflet assembly 10 proximally until prosthetic leaflet assembly 10 contacts first and second suture tubes 56 and 57, as shown in FIG. 4B. Proximal ends 58, 61, and 65 of stylet 55 and first and second suture tubes 56 and 57 then are pulled proximally to compress prosthetic leaflet assembly 10 within the internal lumen of tubing 51 while urging prosthetic leaflet assembly 10 proximally, as depicted in FIG. 4C. To assist in compressing prosthetic leaflet assembly 10, assembly 10 may be cooled and inserted into a loading tube, such as are known in the art. Proximal ends 58, 61, and 65 are pulled proximally until end cap 60 contacts distal end 52 of tubing 51, as shown in FIG. 4D.

Figure 5:
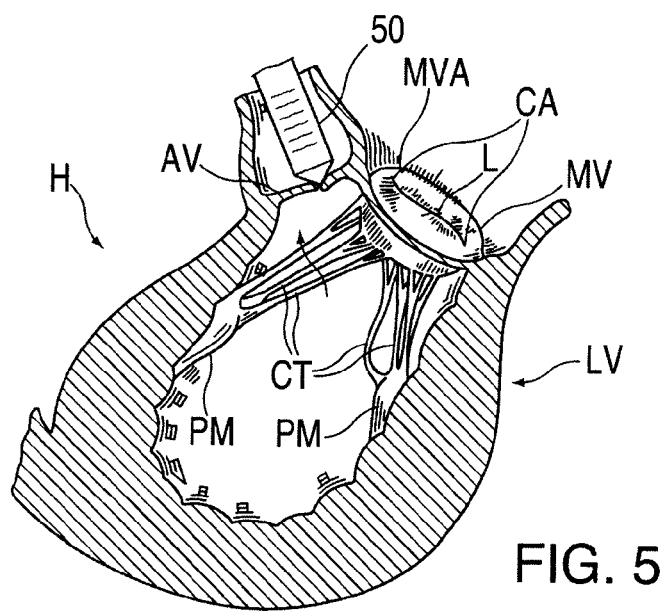
FIG. 5 is a sectional view of the left ventricular portion of a human heart showing a mitral valve being repaired using the prosthetic leaflet assembly system of the present invention, wherein the delivery catheter has been disposed proximate the aortic valve.

Referring to FIG. 5, a method of deploying the prosthetic leaflet assembly of present invention is now described in the context of repairing a defective mitral valve. In FIG. 5, the left ventricular quadrant of a human heart H is shown having a mitral valve MV with commissural areas CA and located within a mitral valve annulus MVA. The leaflets L of the mitral valve MV are tethered to the endocardium of the left ventricle LV via the chordae tendineae CT and papillary muscles PM. The outflow tract of the aortic valve AV is disposed immediately adjacent to the mitral valve MV. This anatomical feature of the mitral valve makes anchoring a prosthetic device directly to the mitral valve annulus problematic, since it creates a risk that prosthetic device will obstruct the outflow tract for the aortic valve. Alternatively, having a prosthetic device expanded into direct engagement with the mitral valve annulus may disrupt or remodel the aortic valve annulus, causing mismatch of the leaflets of that valve and possibly aortic valve regurgitation.

In FIG. 5, delivery catheter 50 is shown approaching the aortic valve AV through the aorta to gain access to the mitral valve MV from below.

Figure 6A:
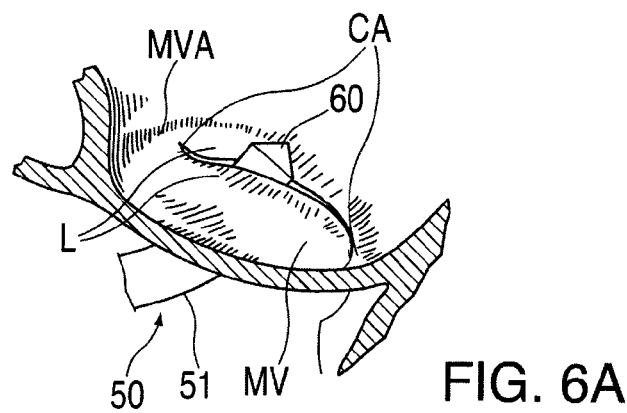
FIGS. 6A through 6E are illustrative views showing deployment of the prosthetic leaflet assembly using the delivery catheter in a mitral valve undergoing repair in accordance with one aspect of the present invention.
Figure 6B:
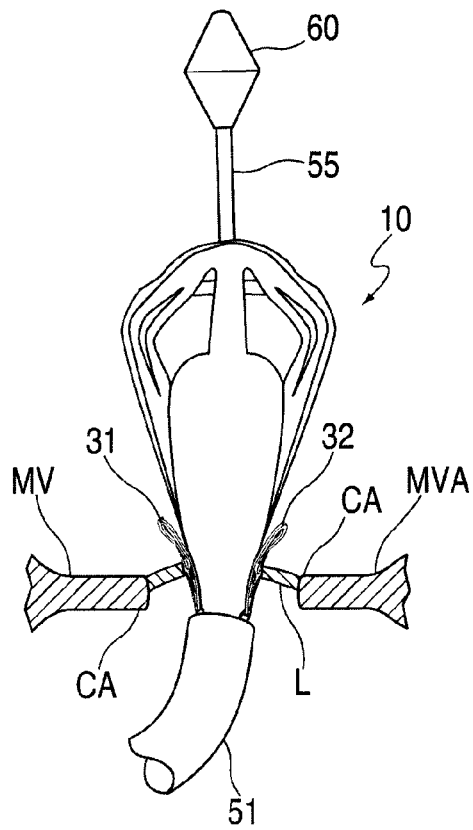
Figure 6C:
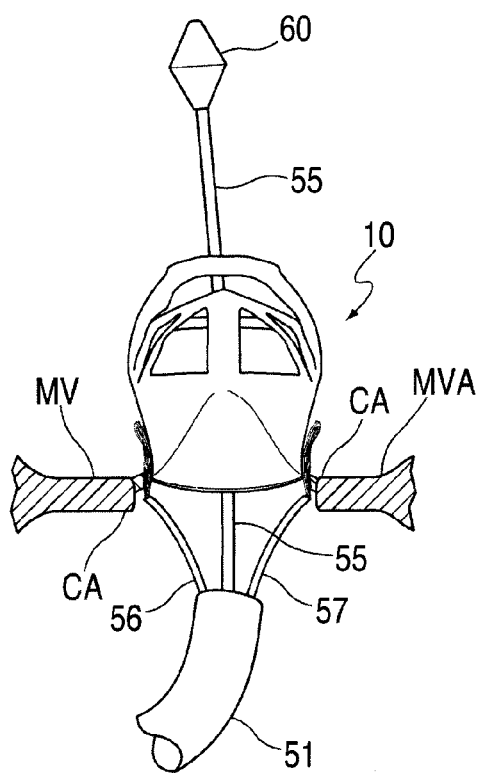

Referring now to FIGS. 6A through 6E, as shown in FIG. 6A, delivery catheter 50 is moved distally until end cap 60 and the distal portion of tubing 51 pass through the leaflets L of the mitral valve MV. Once delivery catheter 50 is disposed partially through the mitral valve MV in a suitable position, as may be determined, e.g., using fluoroscopy, tubing 51 is retracted proximally as shown in FIG. 6B. Delivery catheter 50 may be rotated and moved proximally and distally, e.g., by moving and/or rotating handle 54 of delivery catheter 50, to properly align anchors 31 and 32 of prosthetic leaflet assembly 10 with the predetermined region, e.g., commissural areas CA, of the mitral valve MV, e.g., using fluoroscopic guidance. As tubing 51 of delivery catheter 50 is withdrawn, prosthetic leaflet assembly 10 may expand as depicted in FIG. 6C so that the prosthetic leaflets are deployed within the flow path circumscribed by the native leaflets. First and second suture tubes 56 and 57 may be curved outwardly to assist in expanding prosthetic leaflet assembly 10.

Figure 6D:
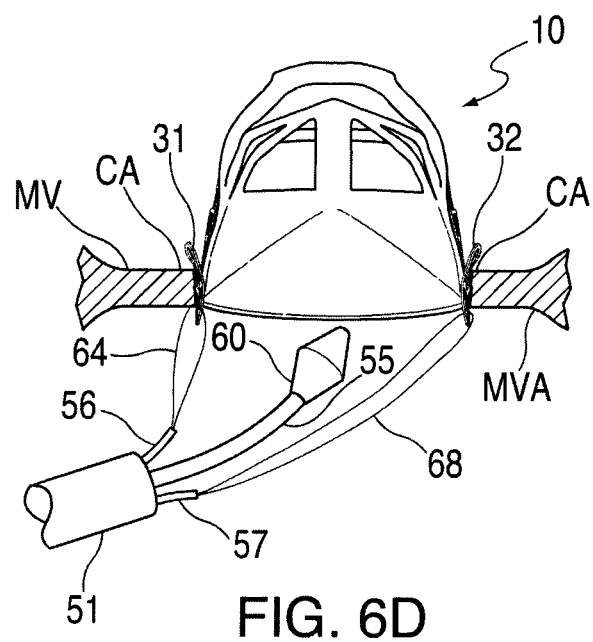

As shown in FIG. 6D, anchors 31 and 32 engage commissural areas CA of the mitral valve MV when the expandable frame of prosthetic leaflet assembly 10 causes the assembly 10 to transition to the expanded deployed state. Anchors 31 and 32 engage predetermined regions of the native valve structure, e.g., commissural areas CA, such that portions of each anchor are located above and/or below the mitral valve annulus MVA.

Figure 6E:
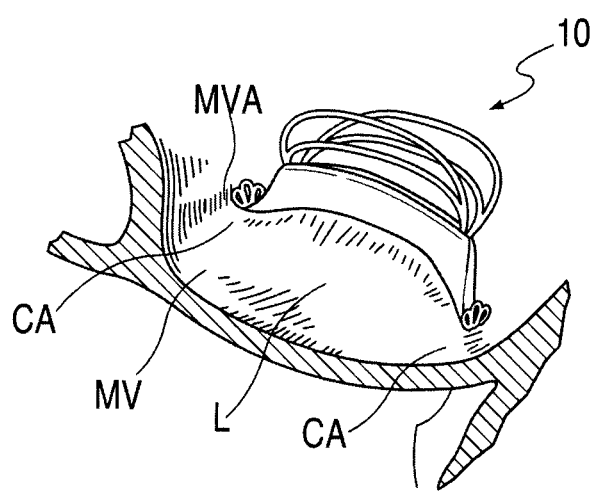

Once prosthetic leaflet assembly 10 is in the expanded deployed state, locking mechanism 63 of first suture tube 56 and locking mechanism 67 of second suture tube 57 may each be released and one end of each suture 64 and 68 may be pulled proximally until each suture is no longer looped around prosthetic leaflet assembly 10, freeing assembly 10. Alternatively, sutures 64 and 68 may be cut using a suitable transvascular tool. Delivery catheter 50 then is fully withdrawn leaving prosthetic leaflet assembly 10 deployed in the mitral valve, as depicted in FIG. 6E. Advantageously, the leaflets L of the mitral valve MV coapt against the expanded deployed prosthetic leaflet assembly 10; illustratively, against the two prosthetic leaflets of prosthetic leaflet assembly 10 such that the two prosthetic leaflets are suspended within the flow path defined by the leaflets L and the prosthetic leaflets coapt with, and improve functioning of, the leaflets L.

In an alternative embodiment, prosthetic leaflet assembly 10 may be implanted with delivery catheter 50 using a minimally-invasive approach wherein delivery catheter 50 is inserted through a keyhole opening in the chest and delivery catheter 50 is inserted transapically from below the mitral valve. As yet another alternative, an open heart surgery approach may be used to gain access to the mitral valve to implant prosthetic leaflet assembly 10. In an embodiment where prosthetic leaflet assembly is implanted using an alternative transvascular approach, implantation of a mitral valve embodiment, for example, may be accomplished by passing delivery catheter 50 through the femoral vein into the right atrium, followed by a transeptal puncture to gain access to the mitral valve from above. In this embodiment, prosthetic leaflet assembly 10 may be loaded in delivery catheter 50 such that stabilization members 33 and 34 and biasing members 37 and 38 of prosthetic leaflet assembly 10 are loaded into delivery catheter 50 first rather than last as depicted in the embodiment of FIGS. 4A through 4D.

As will be appreciated by one of ordinary skill, leaflet assembly 20 may comprise alternative leaflet configurations designed to coapt against the native leaflets, such as balls, flaps, duck-bill elements, etc., such as art known in the art, without departing from the spirit of the present invention, so long as such configurations can be contracted to a reduced delivery state for transcatheter or minimally invasive implantation. In addition, expandable frame 30 may comprise, for example, a suitably trained shape memory alloy, that expands to a deployed shape for use in a non-circular cardiac valve, such as an ovoid or D-shaped configuration. In this latter case, leaflet assembly 20 should be configured so that, when expandable frame 30 is fully deployed, the leaflet assembly expands to a predetermined shape with the required level of coaptation.

Figure 7A:
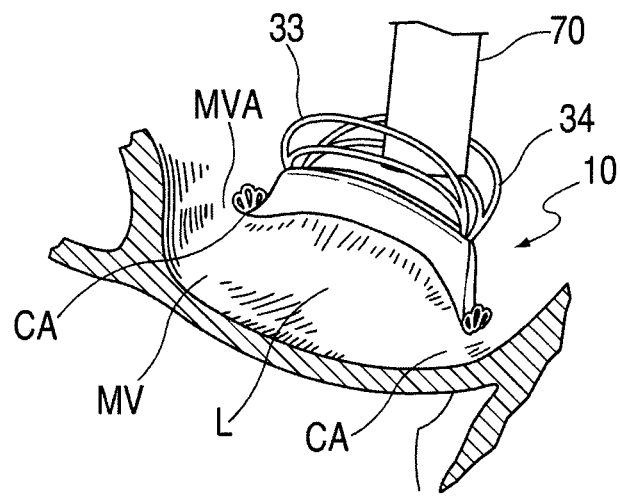
FIGS. 7A and 7B are illustrative views showing deployment of a replacement valve prosthesis at the site of a deployed prosthetic leaflet assembly of the present invention.
Figure 7B:
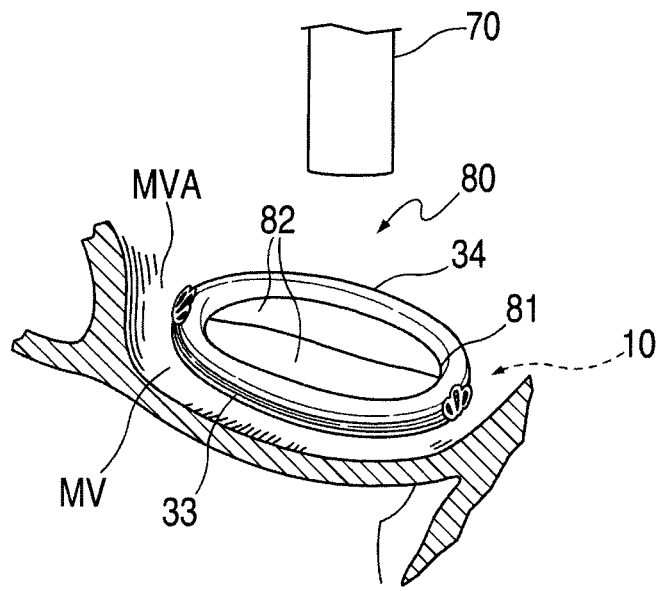

Referring to FIGS. 7A and 7B, a method for deploying a replacement valve prosthesis, such as are known in the art, through the deployed prosthetic leaflet assembly of the present invention is now described. In FIG. 7A, catheter 70 having the replacement valve disposed therein is shown approaching the mitral valve MV wherein catheter 70 is directed, e.g., under fluoroscopic guidance, between stabilization members 33 and 34 of prosthetic leaflet assembly 10. Catheter 70 then is withdrawn and replacement valve prosthesis 80 expands and compresses prosthetic leaflet assembly 10 toward the mitral valve MV, as depicted in FIG. 7B. As replacement valve 80 expands, it preferably engages and anchors to prosthetic leaflet assembly 10. For example, expanding replacement valve 80 may cause the stabilization members and/or biasing members to exert force on valve 80, thereby securing valve 80 within prosthetic leaflet assembly 10. Additionally, replacement valve 80 may be secured to prosthetic leaflet assembly 10 using, for example, sutures or biocompatible adhesive. In turn, because prosthetic leaflet assembly 10 is firmly anchored to the mitral valve MV, replacement valve 80 is anchored at the mitral valve MV.

Replacement valve 80 illustratively is constructed as described in U.S. Pat. No. 4,490,859 to Black et al., which is incorporated herein by reference, and/or the above-mentioned patents to Andersen et al., and comprises treated animal tissue, such as porcine, bovine or equine pericardial tissue, or any of a number of synthetic fabrics, such as a polyethylene terephthalate fabric, e.g., DACRON® (a registered trademark of Invista North America S.A.R.L. Corporation), mounted on a collapsible metal alloy or polymer frame. The collapsible frame 81 may include two or more upstanding posts disposed on the sides of the frame to form commissural points for the tissue or synthetic fabric leaflets 82. As described in the foregoing patent, the tissue or fabric components of the valve body may be cut from flat pieces of material, and then sewn or bonded together, and to the upstanding posts and the frame, to form a valve that mimics the functionality of an intact non-diseased mitral valve. Alternatively, replacement prosthesis 80 may be of any other construction suitable to be collapsed to a reduced diameter so as to permit the prosthetic valve to be delivered via catheter in a contracted delivery state.

Replacement valve 80 may be implanted immediately after prosthetic leaflet assembly 10 is deployed or may be implanted minutes, days, months, or years after prosthetic leaflet assembly 10 is deployed. In one embodiment, replacement valve 80 is implanted because a defective cardiac valve having prosthetic leaflet assembly 10 deployed thereon further degenerates, for example, due to disease progression or aging, such that valve replacement is required. Replacement valve 80 may be implanted using a transcatheter approach, a minimally invasive approach, or an open heart surgery approach.

In accordance with an alternative embodiment of the present invention, expandable frame 30 may be loaded and deployed without leaflet assembly 20 in a manner similar to descriptions above with respect to FIGS. 4-6. In this embodiment, anchors 31 and 32 apply outward force to the annulus, preferably at the commissures of the defective valve, to forcefully ovalize or modify the shape of the annulus to enhance leaflet coaptation and thereby reduce cardiac valve regurgitation.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A prosthetic leaflet assembly for repairing a defective cardiac valve having two or more native leaflets defining a flow path through a central opening of the defective cardiac valve, the prosthetic leaflet assembly comprising:
   an expandable frame configured to transition from a contracted delivery state to an expanded deployed state, the expandable frame having one or more anchors configured to engage a predetermined region of the defective cardiac valve in the expanded deployed state; and
   one or more prosthetic leaflets coupled to the expandable frame, the one or more prosthetic leaflets configured to be suspended within the flow path and to occupy a portion of the central opening such that the one or more prosthetic leaflets coapt with, and improve functioning of, the two or more native leaflets.

2. The prosthetic leaflet assembly of claim 1, wherein the expandable frame further comprises one or more stabilization members configured to be disposed upstream of the defective cardiac valve to prevent the two or more native leaflets from prolapsing and to prevent migration of the prosthetic leaflet assembly.

3. The prosthetic leaflet assembly of claim 1, wherein the expandable frame further comprises one or more biasing members configured to urge the one or more anchors into engagement with the predetermined region.

4. The prosthetic leaflet assembly of claim 1, wherein the one or more anchors comprise first and second anchors, and wherein the one or more prosthetic leaflets are disposed between the first and second anchors.

5. The prosthetic leaflet assembly of claim 1, wherein the predetermined region comprises commissural areas of the defective cardiac valve.

6. The prosthetic leaflet assembly of claim 1, wherein the expandable frame and the one or more prosthetic leaflets are configured to transition between a delivery state enabling transcatheter delivery and an expanded, deployed state.

7. The prosthetic leaflet assembly of claim 1, wherein the prosthetic leaflet assembly is configured to repair one of a mitral valve, a tricuspid valve, an aortic valve, or a pulmonary valve.

8. The prosthetic leaflet assembly of claim 1, wherein the expandable frame is self-expanding.

9. The prosthetic leaflet assembly of claim 8, wherein the expandable frame comprises a nickel-titanium alloy.

10. The prosthetic leaflet assembly of claim 1, wherein the one or more prosthetic leaflets comprise animal tissue.

11. The prosthetic leaflet assembly of claim 10, wherein the animal tissue comprises porcine, equine, or bovine pericardial tissue.

12. The prosthetic leaflet assembly of claim 1, wherein the one or more prosthetic leaflets comprise a synthetic fabric.

13. The prosthetic leaflet assembly of claim 1, wherein the prosthetic leaflet assembly is configured to be delivered transvascularly or transapically using a minimally invasive approach.

14. The prosthetic leaflet assembly of claim 1, wherein the expandable frame is configured to accommodate deployment of a replacement valve, such that the expandable frame serves as an anchor for the replacement valve.

15. The prosthetic leaflet assembly of claim 14, wherein the replacement valve is configured to be implanted seconds, days, months, or years after the prosthetic leaflet assembly is deployed.

16. The prosthetic leaflet assembly of claim 1, wherein the portion that the one or more prosthetic leaflets occupy is between 5 to 35 percent of the central opening of the defective cardiac valve.

17. A method of repairing a defective cardiac valve having two or more native leaflets defining a flow path through a central opening of the defective cardiac valve, the method comprising:

providing a prosthetic leaflet assembly having one or more prosthetic leaflets mounted on an expandable frame, the expandable frame having one or more anchors;

implanting the prosthetic leaflet assembly in a heart having the defective cardiac valve by engaging the one or more anchors to a predetermined region of the defective cardiac valve, such that the one or more prosthetic leaflets are suspended within the flow path and occupy a portion of the central opening such that the one or more prosthetic leaflets coapt with, and improve functioning of, the two or more native leaflets.

18. The method of claim 17, wherein engaging the predetermined region further comprises transitioning the prosthetic leaflet assembly between a delivery state and an expanded, deployed state.

19. The method of claim 17, wherein the expandable frame is self-expanding, and wherein engaging the predetermined region further comprises releasing the self-expanding expandable frame.

20. The method of claim 17, further comprising preventing the two or more native leaflets from prolapsing during systole using one or more stabilization members of the expandable frame disposed upstream of the defective cardiac valve.

* * * * *